US011295445B2

(12) United States Patent
Smith

(10) Patent No.: US 11,295,445 B2
(45) Date of Patent: Apr. 5, 2022

(54) SYSTEMS AND METHODS FOR DETECTION AND STAGING OF PULMONARY FIBROSIS FROM IMAGE-ACQUIRED DATA

(71) Applicant: THE UAB RESEARCH FOUNDATION, Birmingham, AL (US)

(72) Inventor: Andrew Dennis Smith, Hoover, AL (US)

(73) Assignee: THE UAB RESEARCH FOUNDATION, Birmingham, AL (US)

( * ) Notice: Subject to any disclaimer, the term of this patent is extended or adjusted under 35 U.S.C. 154(b) by 0 days.

(21) Appl. No.: 17/223,178

(22) Filed: Apr. 6, 2021

(65) Prior Publication Data

US 2021/0224987 A1    Jul. 22, 2021

Related U.S. Application Data

(63) Continuation of application No. PCT/US2020/056679, filed on Oct. 21, 2020.
(Continued)

(51) Int. Cl.
*G06T 7/00* (2017.01)
*G06T 7/13* (2017.01)
(Continued)

(52) U.S. Cl.
CPC .............. *G06T 7/0012* (2013.01); *G06T 7/13* (2017.01); *G16H 50/20* (2018.01); *G16H 50/30* (2018.01);
(Continued)

(58) Field of Classification Search
None
See application file for complete search history.

(56) References Cited

U.S. PATENT DOCUMENTS 10,130,295 B2 * 11/2018 Smith ................ A61B 8/485
2013/0121545 A1    5/2013 Zhou et al.
(Continued)

FOREIGN PATENT DOCUMENTS

WO    2019/102829 A1    5/2019

OTHER PUBLICATIONS

Hu, Shiying, Eric A. Hoffman, and Joseph M. Reinhardt. "Automatic lung segmentation for accurate quantitation of volumetric X-ray CT images." IEEE transactions on medical imaging 20.6 (2001): 490-498. (Year: 2001).*
(Continued)

*Primary Examiner* — Samah A Beg
(74) *Attorney, Agent, or Firm* — Workman Nydegger

(57) ABSTRACT

A method for ascertaining pulmonary fibrosis disease progression or treatment response includes obtaining a first set of computed tomography (CT) images of a lung and determining a first Pulmonary Surface Index (PSI) score for the lung by detecting a first actual lung boundary of the lung within the first set of CT images, determining a first approximated lung boundary within the first set of CT images, and determining the PSI score using inputs based on the first actual lung boundary and the first approximated lung boundary. The method also includes obtaining a second set of CT images of the lung and determining a second PSI score for the lung using inputs based on a second actual lung boundary and a second approximated lung boundary. The method also includes assessing pulmonary fibrosis treatment response or disease progression based on the first PSI score and the second PSI score.

9 Claims, 8 Drawing Sheets

Related U.S. Application Data

(60) Provisional application No. 62/924,144, filed on Oct. 21, 2019.

(51) Int. Cl.
   *G16H 50/30* (2018.01)
   *G16H 50/20* (2018.01)

(52) U.S. Cl.
   CPC .............. *G06T 2207/10081* (2013.01); *G06T 2207/30064* (2013.01)

(56) References Cited

U.S. PATENT DOCUMENTS

| | | | | |
|---|---|---|---|---|
| 2015/0148658 A1* | 5/2015 | Smith | ................... | A61B 5/055 600/410 |
| 2017/0109893 A1 | 4/2017 | Cong et al. | | |
| 2017/0261584 A1* | 9/2017 | James | ................ | G01R 33/4835 |
| 2019/0083024 A1* | 3/2019 | Smith | ................... | A61B 8/485 |

OTHER PUBLICATIONS

Lafata, Kyle J., et al. "An exploratory radiomics approach to quantifying pulmonary function in CT images." Scientific reports 9.1 (2019): 1-9. (Year: 2019).*

Jacob, Joseph, et al. "Mortality prediction in idiopathic pulmonary fibrosis: evaluation of computer-based CT analysis with conventional severity measures." European Respiratory Journal 49.1 (2017). (Year: 2017).*

Wells, Athol U., et al. "Idiopathic pulmonary fibrosis: a composite physiologic index derived from disease extent observed by computed tomography." American journal of respiratory and critical care medicine 167.7 (2003): 962-969. (Year: 2003).*

International Search Report and Written Opinion received for PCT Patent Application No. PCT/US2020/056679, dated Jan. 25, 2021, 9 pages.

* cited by examiner

SYSTEMS AND METHODS FOR DETECTION AND STAGING OF PULMONARY FIBROSIS FROM IMAGE-ACQUIRED DATA

CROSS REFERENCE TO RELATED APPLICATIONS

This application is a continuation of International Patent Application No. PCT/US20/56679, filed Oct. 21, 2020, which claims the benefit of U.S. Provisional Application No. 62/924,144, filed Oct. 21, 2019, which are incorporated by reference in their entirety.

BACKGROUND

Pulmonary fibrosis refers to the progressive scarring of the lungs. The accumulation of fibrous connective tissue causes lung stiffness, decreased lung volumes, and reduces the oxygen supply in the blood, resulting in shortness of breath. Pulmonary fibrosis may occur as a secondary effect of another disease or condition, such as inhalation of pollutants, hypersensitivity pneumonitis, autoimmune disorders, viral infections, and/or bacterial infections (e.g., tuberculosis). Additionally, in some instances, pulmonary fibrosis may occur without an identifiable cause. Such cases are diagnosed as idiopathic pulmonary fibrosis (IPF). Although research is ongoing, there is no evidence that any medications can successfully treat IPF, leaving lung transplant as the leading therapeutic option available in many cases. Without a lung transplant, IPF typically results in death.

Although there is no formal staging system for pulmonary fibrosis, current staging is performed by lung biopsy or by evaluating symptoms, pulmonary function tests (PFTs), exercise capacity, and/or high-resolution computed tomography (HRCT). In some instances, the Gender-Age-Physiology (GAP) score or the du Bois score have been used to stage disease severity in the research setting. Conventional staging systems, however, fail to provide sufficient score granularity to make them clinically beneficial for evaluating treatment response, analyzing disease progression, or determining useful staging for pulmonary fibrosis.

As pulmonary fibrosis progresses, retraction of the lung surface occurs, leading to an irregular and nodular or bumpy surface. However, current quantitative CT biomarkers lack sufficient accuracy to predict the progression of pulmonary fibrosis based on irregularities on the lung surface. Because CT image evaluation is subjective, experts may disagree on progression classification in many cases. Similarly, because CT image evaluation is subjective, experts may disagree when classifying pulmonary fibrosis disease progression or treatment response based on analysis of CT images taken at different timepoints.

Additionally, ultrasound imaging fails to provide a basis for quantifying the progression of lung surface irregularities/nodularity. Furthermore, magnetic resonance imaging (MRI) fails to capture lung surface in a way that provides a basis for making even a qualitative analysis of lung surface irregularity/nodularity.

Accordingly, there are a number of disadvantages with current methods for staging pulmonary fibrosis.

BRIEF SUMMARY

Implementations of the present disclosure are directed to systems and methods for detection, staging, and/or assessing disease progression or treatment response of pulmonary fibrosis from image-acquired data.

In one aspect, a computer-implemented method for ascertaining pulmonary fibrosis disease progression or treatment response includes obtaining a first set of computed tomography (CT) images of a lung. The first set of CT images of the lung is associated with a first timepoint. The method also includes determining a first Pulmonary Surface Index (PSI) score for the lung. Determining the first PSI score for the lung includes detecting a first actual lung boundary of the lung within the first set of CT images. The first actual lung boundary extends about at least a first perimeter of the lung. Determining the first PSI score also includes determining a first approximated lung boundary within the first set of CT images. The first approximated lung boundary extends about at least the first perimeter of the lung, and the first approximated lung boundary comprises a representation of a smooth lung boundary for the first perimeter of the lung. The first PSI score for the lung is determined using inputs based on the first actual lung boundary and the first approximated lung boundary.

The method also includes obtaining a second set of CT images of the lung, where the second set of CT images of the lung is associated with a second timepoint, which is different than the first timepoint. The method also includes determining a second PSI score for the lung, which includes detecting a second actual lung boundary of the lung within the second set of CT images (where the second actual lung boundary extends about at least a second perimeter of the lung), determining a second approximated lung boundary within the second set of CT images (where the second approximated lung boundary extends about at least the second perimeter of the lung, and the second approximated lung boundary comprises a representation of a smooth lung boundary for the second perimeter of the lung), and determining the second PSI score for the lung using inputs based on the second actual lung boundary and the second approximated lung boundary.

The method also includes assessing pulmonary fibrosis treatment response or disease progression for the lung based on the first PSI score and the second PSI score.

In another aspect, a computer-implemented method for ascertaining stage severity of pulmonary fibrosis, includes obtaining a set of computed tomography (CT) images of a lung and identifying a lung boundary from the set of CT images. The method also includes calculating a Pulmonary Surface Index (PSI) score for the lung boundary from the set of CT images. Calculating the PSI score includes fitting a spline to the lung boundary in the set of CT images, determining a distance between the lung boundary and the spline at each pixel of the lung boundary in the set of CT images, and determining a mean distance or a median distance between the lung boundary and the spline in the set of CT images. The method also includes obtaining a pulmonary function metric associated with the lung based on a result of a pulmonary function test performed for the lung. The method further includes determining a stage severity of lung fibrosis for the lung based on at least the PSI score and the pulmonary function metric.

This summary is provided to introduce a selection of concepts in a simplified form that are further described below in the detailed description. This summary is not intended to identify key features or essential features of the claimed subject matter, nor is it intended to be used as an indication of the scope of the claimed subject matter. The features and advantages of the disclosure may be realized and obtained by means of the instruments and combinations particularly pointed out in the appended claims. These and other features of the present disclosure will become more fully apparent from the following description and appended claims or may be learned by the practice of the disclosure as set forth hereinafter.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope. The disclosure will be described and explained with additional specificity and detail through the use of the accompanying drawings, in which.

DETAILED DESCRIPTION

Figure 1:
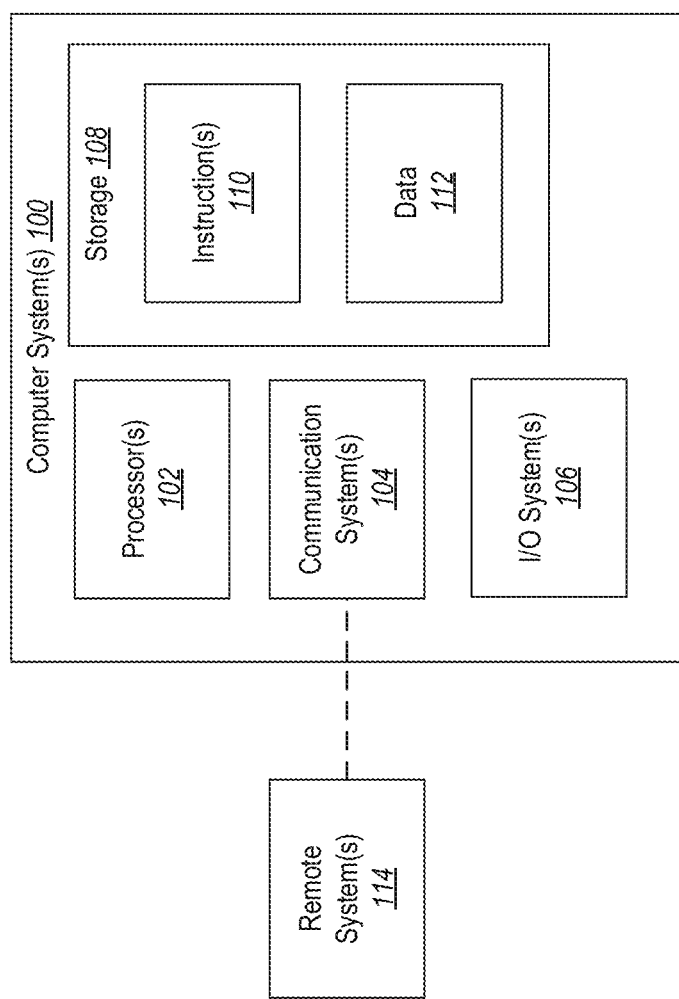
FIG. 1 illustrates an example computer system that may comprise or implement one or more embodiments of the present disclosure.

Before describing various embodiments of the present disclosure in detail, it is to be understood that this disclosure is not limited to the parameters of the particularly exemplified systems, methods, apparatus, products, processes, and/or kits, which may, of course, vary. Thus, while certain embodiments of the present disclosure will be described in detail, with reference to specific configurations, parameters, components, elements, etc., the descriptions are illustrative and are not to be construed as limiting the scope of the claimed invention. In addition, any headings used herein are for organizational purposes only, and the terminology used herein is for the purpose of describing the embodiments. Neither are not meant to be used to limit the scope of the description or the claims.

Implementations of the present disclosure are directed to systems and methods for detection, staging, and/or assessing disease progression or treatment response of pulmonary fibrosis from image-acquired data.

In some embodiments, a computer-implemented method for ascertaining pulmonary fibrosis disease progression or treatment response includes obtaining a first set of computed tomography (CT) images of a lung. The first set of CT images of the lung is associated with a first timepoint. The method also includes determining a first Pulmonary Surface Index (PSI) score for the lung. Determining the first PSI score for the lung includes detecting a first actual lung boundary of the lung within the first set of CT images. The first actual lung boundary extends about at least a first perimeter of the lung. Determining the first PSI score also includes determining a first approximated lung boundary within the first set of CT images. The first approximated lung boundary extends about at least the first perimeter of the lung, and the first approximated lung boundary comprises a representation of a smooth lung boundary for the first perimeter of the lung. The first PSI score for the lung is determined using inputs based on the first actual lung boundary and the first approximated lung boundary.

The method also includes obtaining a second set of CT images of the lung, where the second set of CT images of the lung is associated with a second timepoint, which is different than the first timepoint. The method also includes determining a second PSI score for the lung, which itself includes detecting a second actual lung boundary of the lung within the second set of CT images (where the second actual lung boundary extends about at least a second perimeter of the lung), determining a second approximated lung boundary within the second set of CT images (where the second approximated lung boundary extends about at least the second perimeter of the lung, and the second approximated lung boundary comprises a representation of a smooth lung boundary for the second perimeter of the lung), and determining the second PSI score for the lung using inputs based on the second actual lung boundary and the second approximated lung boundary.

The method also includes assessing pulmonary fibrosis treatment response or disease progression for the lung based on the first PSI score and the second PSI score.

In another aspect, a computer-implemented method for ascertaining stage severity of pulmonary fibrosis, includes obtaining a set of computed tomography (CT) images of a lung and identifying a lung boundary from the set of CT images. The method also includes calculating a Pulmonary Surface Index (PSI) score for the lung boundary from the set of CT images. Calculating the PSI score includes fitting a spline to the lung boundary in the set of CT images, determining a distance between the lung boundary and the spline at each pixel of the lung boundary in the set of CT images, and determining a mean distance or a median distance between the lung boundary and the spline in the set of CT images. The method also includes obtaining a pulmonary function metric associated with the lung based on a result of a pulmonary function test performed for the lung. The method further includes determining a stage severity of lung fibrosis for the lung based on at least the PSI score and the pulmonary function metric.

As noted hereinabove, conventional staging systems fail to provide sufficient granularity to make them clinically beneficial for evaluating treatment response, analyzing disease progression, and/or determining useful staging for pulmonary fibrosis. For example, a GAP score includes points assigned to various risk factors (with a maximum point value of 8) and defines three disease stages based on the number of points assigned to a patient. However, a three-stage system often fails to provide significant clinical benefits. For instance, a three-stage system provides overly broad classifications into which patients may fall and fails to provide for meaningful differentiation of patients within each stage (e.g., where such differentiations might give rise to different treatment options may be more narrowly tailored to patient needs). As another example, a patient classified as experiencing stage two pulmonary fibrosis may undergo significant disease progression before becoming classifiable as experiencing stage three pulmonary fibrosis. Thus, a GAP score may fail to provide medical practitioners with sufficiently granular disease progression information to allow practitioners to tailor treatment decisions based on small steps in disease progression (e.g., causing practitioners to tailor treatment decisions only based on large steps in disease progression, which may cause avoidable delay in modifying treatment).

As another example, the du Bois score assigns points to various risk factors to predict an expected one-year probability of death. For reasons similar to those described above for the GAP score, the du Bois score fails to provide sufficiently granular information to make it clinically beneficial for evaluating treatment response, analyzing disease progression, or determining useful staging for pulmonary fibrosis.

Those skilled in the art will appreciate, in view of the present disclosure, that at least some of the disclosed embodiments may address deficiencies associated with detection, staging, and/or analyzing disease progression or treatment response of pulmonary fibroses. At least some of the disclosed embodiments may provide a non-invasive yet rigorous methodology for detecting, staging the severity of, and/or analyzing disease progression or treatment response of pulmonary fibrosis. The disclosed embodiments may also provide a Pulmonary Surface Index (PSI) score, which comprises a quantitative, continuous numeric value that may represent the degree of lung surface irregularity that correlates with the severity of pulmonary fibrosis or emphysema. Such a PSI score may be used, in contrast with existing staging techniques, to provide a granular representation of disease state and progression (e.g., for longitudinal analysis) of pulmonary fibrosis, which may enable practitioners to assess treatment response and/or make intelligent treatment decisions that are more narrowly tailored to the needs of patients.

Furthermore, the disclosed embodiments may provide a system that utilizes highly standardizable quantitative methods for image acquisition and processing, allowing for uniformity in staging. The disclosed systems and methods may also provide a staging process that includes short scan times with rapid, reliable quantitative analysis of the medical images at low cost.

Additionally, the disclosed embodiments may be implemented with routine CT medical images, which are widely available at medical centers that treat patients with pulmonary fibrosis. Thus, the disclosed embodiments may provide significant benefits in the field of detecting and treating pulmonary fibrosis without requiring specialized imaging processes or equipment. For example, the disclosed embodiments may be implemented using CT images that were previously acquired for subject patients, as well as newly acquired CT images for the subject patients. Such features may provide practitioners the ability to identify disease progression of subject patients using retroactively acquired CT images to inform current treatment decisions (e.g., immediately after beginning implementation of the disclosed embodiments).

Still furthermore, the disclosed embodiments may allow for multiple imaging measurements on the same patient's medical images, providing a sample of the entire lung surface.

Having described some of the various high-level features and benefits of the disclosed embodiments, attention will now be directed to FIGS. 1 through 7. These FIGS. illustrate various conceptual representations, architectures, methods, and/or supporting illustrations related to the disclosed embodiments.

FIG. 1 illustrates an example computer system 100 that may comprise or implement one or more embodiments of the present disclosure. As is illustrated in FIG. 1, the computer system 100 includes processor(s) 102, communication system(s) 104, I/O system(s) 106, and storage 108. Although FIG. 1 illustrates the computer system 100 as including particular components, it will be appreciated, in view of the present disclosure, that a computer system 100 may comprise any number of additional or alternative components.

The processor(s) 102 may comprise one or more sets of electronic circuitry that include any number of logic units, registers, and/or control units to facilitate the execution of computer-readable instructions (e.g., instructions that form a computer program). Such computer-readable instructions may be stored within storage 108. The storage 108 may comprise physical system memory and may be volatile, non-volatile, or some combination thereof. Furthermore, storage 108 may comprise local storage, remote storage, or some combination thereof. Additional details related to processors (e.g., processor(s) 102) and computer storage media (e.g., storage 108) will be provided hereinafter.

As used herein, processor(s) 102 may comprise or be configurable to execute any combination of software and/or hardware components that are operable to facilitate processing using machine learning models or other artificial intelligence-based structures/architectures. For example, processor(s) 102 may comprise and/or utilize hardware components or computer-executable instructions operable to carry out function blocks and/or processing layers configured in the form of, by way of non-limiting example, single-layer neural networks, feed forward neural networks, radial basis function networks, deep feed-forward networks, recurrent neural networks, long-short term memory (LSTM) networks, gated recurrent units, autoencoder neural networks, variational autoencoders, denoising autoencoders, sparse autoencoders, Markov chains, Hopfield neural networks, Boltzmann machine networks, restricted Boltzmann machine networks, deep belief networks, deep convolutional networks (or convolutional neural networks), deconvolutional neural networks, deep convolutional inverse graphics networks, generative adversarial networks, liquid state machines, extreme learning machines, echo state networks, deep residual networks, Kohonen networks, support vector machines, neural Turing machines, and/or others.

As will be described in more detail, the processor(s) 102 may be configured to execute instructions 110 stored within storage 108 to perform certain actions associated with detecting, staging, and/or analyzing treatment response or disease progression of pulmonary fibrosis. The actions may rely at least in part on data 112 stored on storage 108 in a volatile or non-volatile manner. In some instances, the actions may rely at least in part on communication system(s) 104 for receiving data from remote system(s) 114, which may include, for example, other computer systems or computing devices, medical imaging devices/systems, and/or others.

The communications system(s) 104 may comprise any combination of software or hardware components that are operable to facilitate communication between on-system components/devices and/or with off-system components/devices. For example, the communications system(s) 104 may comprise ports, buses, or other physical connection apparatuses for communicating with other devices/components (e.g., USB port, SD card reader, and/or other apparatus). Additionally, or alternatively, the communications system(s) 104 may comprise systems/components operable to communicate wirelessly with external systems and/or devices through any suitable communication channel(s), such as, by way of non-limiting example, Bluetooth, ultra-wideband, WLAN, infrared communication, and/or others.

Furthermore, in some instances, the actions that are executable by the processor(s) 102 may rely at least in part on I/O system(s) 106 for receiving user input from one or more users. I/O system(s) 106 may include any type of input or output device such as, by way of non-limiting example, a touch screen, a display, a mouse, a keyboard, a controller, and/or others, without limitation.

Figure 2:
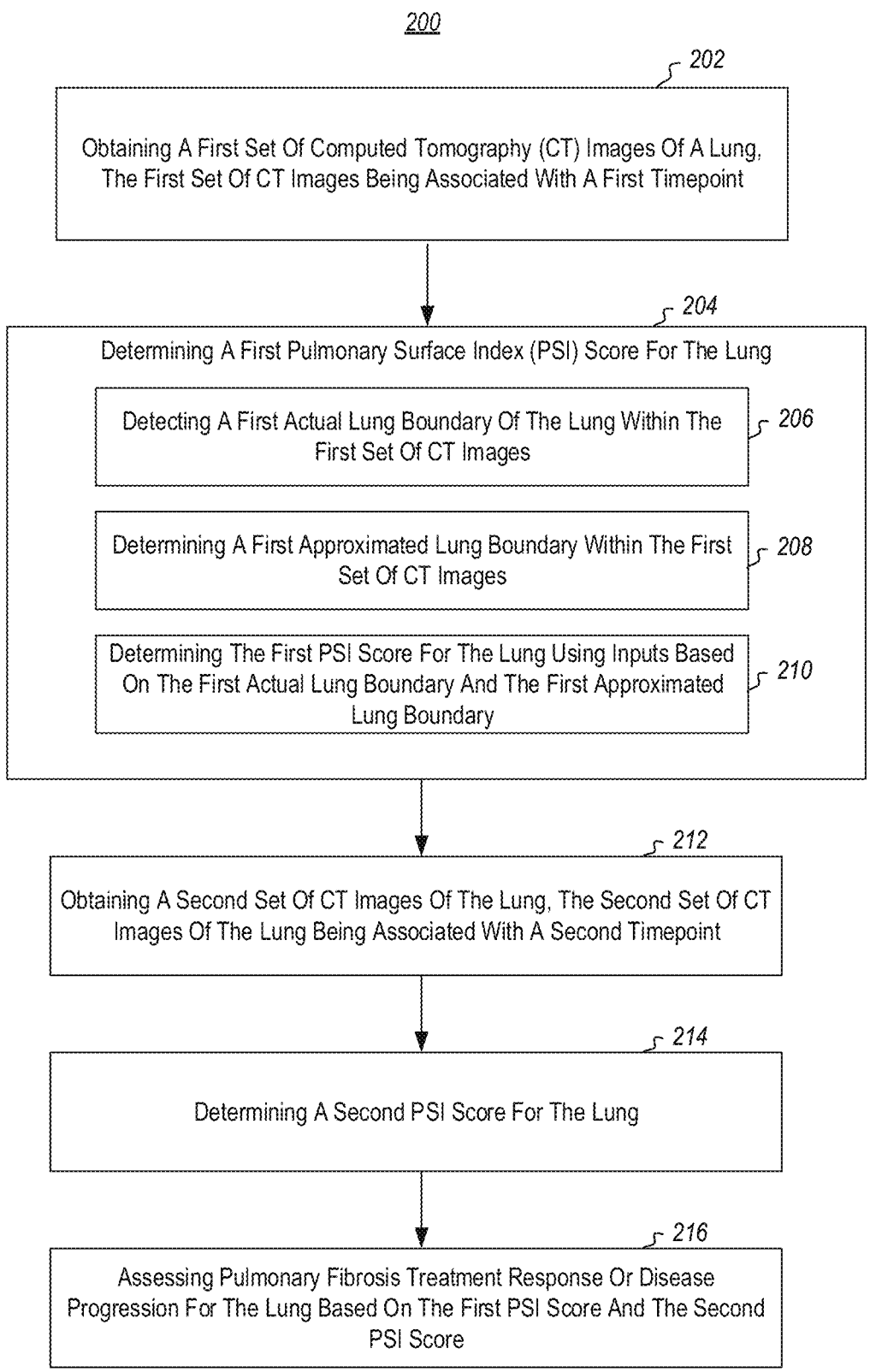
FIG. 2 illustrates an example flow diagram depicting acts associated with ascertaining pulmonary fibrosis disease progression or treatment response.

Some embodiments of the present disclosure can also be described in terms of acts (e.g., acts of a method) for accomplishing a particular result. Along these lines, FIG. 2 illustrates an example flow diagram 200 depicting acts associated with ascertaining pulmonary fibrosis disease progression or treatment response. Although the acts shown in flow diagram 200 may be illustrated and/or discussed in a certain order, no particular ordering is required unless specifically stated or required because an act is dependent on another act being completed prior to the act being performed. Furthermore, it should be noted that not all acts represented in flow diagram 200 are essential for ascertaining pulmonary fibrosis disease progression or treatment response.

In some instances, the various acts disclosed herein are performed using a computer system 100. For instance, code for configuring the computer system 100 to perform the various acts disclosed herein may be stored as instructions 110 on storage 108, and such instructions 110 may be executable by the processor(s) 102 (and/or other components) to facilitate carrying out of the various acts.

Act 202 of flow diagram 200 includes obtaining a first set of computed tomography (CT) images of a subject lung, the first set of CT images being associated with a first timepoint. In some embodiments, the CT images are in Digital Imaging and Communications in Medicine (DICOM) format, and the CT images may comprise conventional CT images, high resolution CT (HRCT) images, and/or other medical images. Furthermore, the first set of CT images may comprise any number of CT images (e.g., one or more than one), and the first timepoint that the first set of CT images is associated with may be regarded as a general timepoint at which the first set of CT images is/was captured (e.g., a time of a particular patient visit or imaging session) or a set of timepoints that corresponds to image capture timestamps for each CT image of the first set of CT images.

Figure 3:
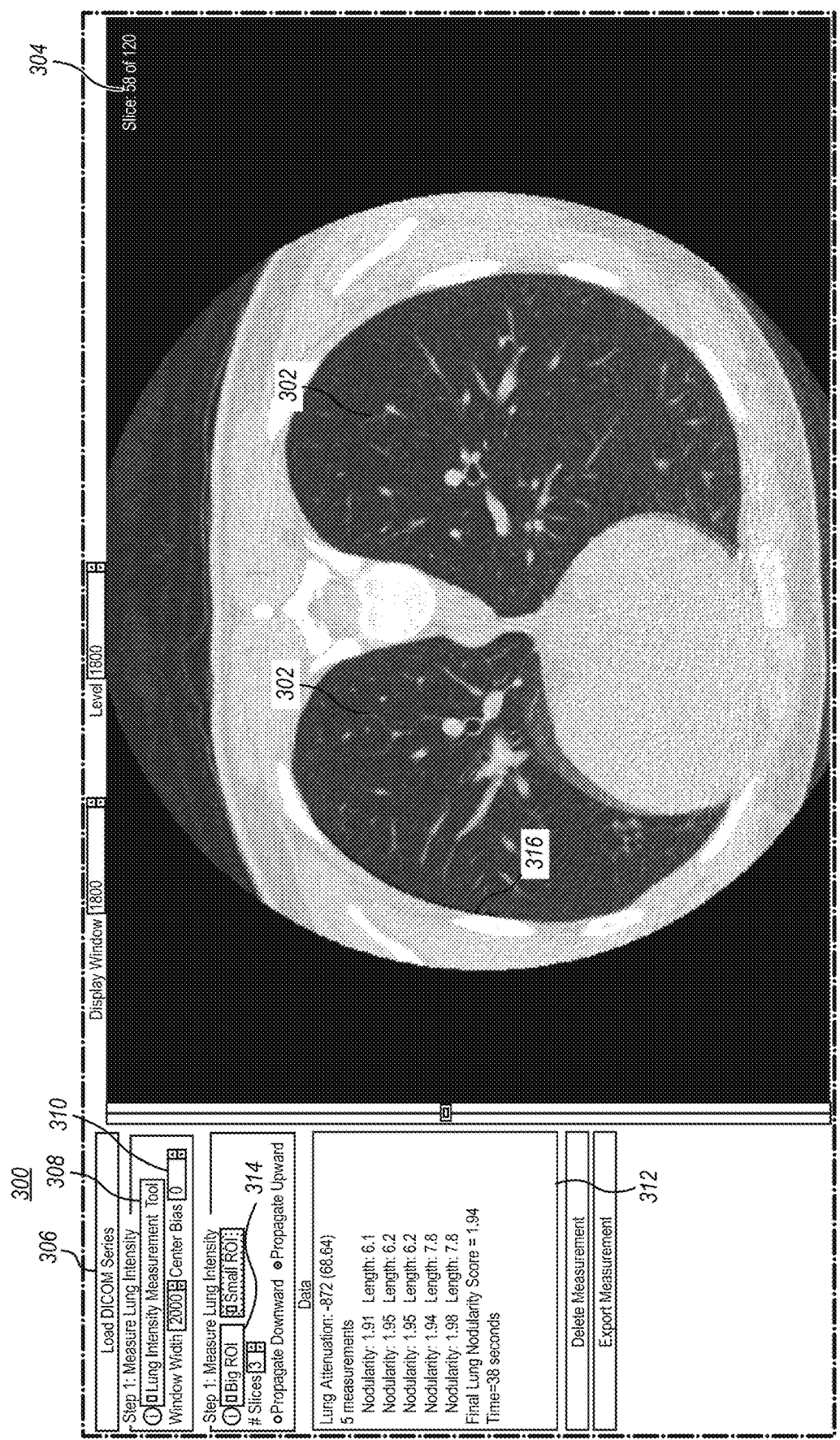
FIG. 3 illustrates an example rendering of various components of a user interface for determining a Pulmonary Surface Index (PSI) score using one or more high resolution computed tomography (HRCT) images of a subject not experiencing pulmonary fibrosis.

For example, FIG. 3 illustrates an example rendering of various components of a user interface 300 for determining a Pulmonary Surface Index (PSI) score using one or more high resolution computed tomography (HRCT) images of lungs 302 of a subject not experiencing pulmonary fibrosis. A computer system 100 as in FIG. 1 may store instructions for executing and presenting the user interface 300 to a user to enable the user to interact with the user interface (e.g., via I/O system(s) 306). FIG. 3 more particularly illustrates a first set of CT images 304 and displays a single slice of a plurality of slices. User interface 300 also displays a "Load DICOM Series" button 306, which may be operable to obtain a set of CT images (e.g., the first set of CT images 304). In some instances, the first set of CT images 304 is obtained directly from an imaging system (e.g., a remote system 314) or from local or remote storage 308.

Act 204 of flow diagram 200 includes determining a first Pulmonary Surface Index (PSI) score for the lung. The PSI score may comprise a continuous numeric value that provides a measurement of the outward projections, inward retractions and overall irregularity of the lung surface that are caused by the formation and accumulation of scar tissue in the lungs associated with pulmonary fibrosis. For an individual with a nodular lung surface, the greater the deviation of the outward projections and inward retractions are from an expected smooth lung surface and the greater the overall irregularity of the lung surface, the larger the PSI score.

FIG. 2 illustrates that determining a first pulmonary surface index score for the lung according to act 204 may be associated with various additional acts. For example, act 206 associated with act 204 of flow diagram 200 includes detecting a first actual lung boundary of the lung within the first set of CT images. The first actual lung boundary extends about at least a first perimeter of the lung. The lung boundary is defined as the outer portion of the lung that is in contact with other adjacent organs and tissues. As used herein "actual" in "actual lung boundary" refers to a representation of a physical lung boundary as captured in a medical image (e.g., as captured within the first set of CT images 304).

Referring again to FIG. 3, pursuant to detecting the first actual lung boundary of the lung within the first set of CT images in accordance with act 206, the user interface 300 may display the first set of CT images 304 in navigable form. For instance, FIG. 3 shows the user interface 300 displaying slice 58 of the first set of CT images 304 in DICOM, grayscale format. A user may navigate (e.g., by scrolling, magnifying, panning, etc.) through the first set of CT images 304 within the user interface 300 to identify slices from the first set of CT images 304 that present a suitable actual lung boundary for detection in accordance with act 206. For example, a user may scroll through the images to identify images that include sites where the contrast between the lung boundary and surrounding tissue appears favorable for detecting the edge of the lung (as will be described hereinbelow).

In some embodiments, a computer system 100 (e.g., FIG. 1) provides functionality for applying denoising filters/processes to one or more slices of the first set of CT images 304, which may reduce the influence of noisy pixels on lung boundaries in lower quality scans. This functionality may be automatically applied, or may be activatable by user input (e.g., via a button within the user interface 300). Such denoising operations may improve the accuracy of final PSI score measurements. Noise reduction techniques may comprise any noise reduction algorithms known in the art and/or deep learning image reconstruction or other AI-based techniques.

Using identified candidate slices for detecting a first actual lung boundary, a computer system 100 may be configurable to apply an edge detecting filter to at least a portion of the first set of CT images 304 (pursuant to act 206). The edge detecting filter may be operable to identify pixels along a high-contrast interface between the lungs 302 and surrounding tissue.

In many instances, the attenuation of a lung within a CT image is sufficiently lower than the attenuation for surrounding tissue (resulting in different pixel intensities for the lung edge and the surrounding tissue), even for lungs suffering from pulmonary fibrosis. Such contrast is evident between lungs 302 as shown in FIG. 3 and the tissue that surrounds FIG. 3. Accordingly, an attenuation range may be preset or predefined for identifying/detecting the boundary of the lung.

In some instances, the user interface 300 may provide functionality for enabling a user to define and/or adjust the attenuation value or range for detecting the first actual lung boundary. For example, FIG. 3 illustrates the user interface 300 as including a "Lung Intensity Measurement Tool" button 308 that may enable users to activate a tool that allows users to select portions of the lungs 302 represented from the first set of CT images 304 to obtain a reference attenuation value or range for detecting the first actual lung boundary. FIG. 3 also shows user interface 300 as including a data window 312 that may be configured to display the predefined or selected attenuation value or range.

User interface 300 also includes input regions 310 to allow users to employ various windowing and/or centering of the images to enhance lung boundary detection. In some instances, as indicated above, windowing and/or centering may be preset or predetermined based on various factors, such as the type of CT image(s) included in the first set of CT images 304 (e.g., non-contrast, contrast-enhanced, high-resolution, etc.).

Pursuant to act 206, based on the attenuation value or range (whether predetermined, user-selected, or automatically determined by the computer system 100), the computer system 100 may be configurable to apply the edge detection filter to one or more images from the first set of CT images 304. The edge detection filter may operate on the grayscale images and may produce an edge mask where only pixels along the high-contrast interface between the lung and surrounding tissue are identified/included. Such filtering may optimize the grayscale images for detecting the first actual lung boundary. The edge detection filter may utilize any suitable edge detection technique or algorithm (e.g., using any suitable thresholding and windowing techniques to optimize contrast between the lungs 302 and adjacent structures). Edge detection operations that rely on artificial intelligence (e.g., machine or deep learning models) are also within the scope of this disclosure.

In some instances, one or more parameters of the edge detection filter are selectively modifiable (e.g., by a user or automatically by the computer system 100). For example, edge sensitivity, which determines how well "weak" edges are detected, can be adjusted by the user. In some embodiments, 12 different edge sensitivities (or any number of different edge sensitivities) may be chosen for each detected lung boundary. As will be described hereinafter, different PSI scores may be generated using different edge detection filtering settings, and a final PSI score may be selected or derived from the different PSI scores generated using different edge detection filtering settings (e.g., edge sensitivity).

Before, after, or contemporaneously with applying the edge detection filter to identify pixels along a high-contrast interface between the lungs 302 and surrounding tissue, detecting the first actual lung boundary of the lungs within the first set of CT images 304 in accordance with act 206 may include obtaining a selection of a portion of the pixels along the high-contrast interface between the lungs 302 and the surrounding tissue. For example, in some instances, the computer system 100 may be configurable to enable users to provide a user selection of a portion of pixels along the high-contrast interface between the lungs 302 and the surrounding tissue using a user-operated brush tool. For instance, FIG. 3 illustrates the user interface 300 as including ROI tools 314, which includes a "Big ROI" button and a "Small ROI" button (where ROI represents a "region of interest"). The different ROI buttons may activate a user tool that allows users to paint or brush (with brush heads of different sizes) along visible boundaries of the lungs 302 as represented within the first set of CT images 304. In this way, users may choose or mark portions about the surface of the lungs 302 that the user desires for forming a basis calculating PSI scores (as will be described hereinbelow).

The user interface 300 may advise users to choose locations about the perimeter of the lungs 302 that appear continuous, and users may be advised to avoid natural sharp edges. Users may utilize the selection tool to select any number of portions (e.g., one or more portions) of lung boundary within a single slice or multiple slices of the first set of CT images 304. Such selections may be operable to provide a selection of a portion of the pixels along the high-contrast interface between the lungs 302 and the surrounding tissue. In some instances, to improve accuracy of calculated PSI scores, users may be advised or required to make one or more selections of actual lung boundaries that form a total length that satisfies a predetermined length condition (e.g., 10 cm or greater) and/or a predetermined number of slices (e.g., 3 or more). The length of the lung boundary pixel selections provided by user input may be displayed within the data window 312, as shown in FIG. 3. In a preferred embodiment, a PSI score is calculated for each of a plurality of slices and the average PSI score is calculated as an overall measure of lung health. That is, the mean PSI score can inform the stage severity of pulmonary fibrosis alone or in combination with other clinical factors, as described herein.

For example, the brushed/selected portions may also be treated as a user-defined lung boundary mask, and this user-defined lung boundary mask may be intersected with the edge mask described hereinabove as being obtained by applying the edge detection filter. The intersection of the masks may exclude all regions of the applicable slices of the first set of CT images 304 that fall outside of the intersection of the edge mask with the user-defined lung boundary mask.

Although the present description has focused, in at least some respects, on implementations in which the computer system 100 applies the edge detection filter prior to obtaining a user selection of a region along an edge of a lung, those skilled in the art will recognize, in view of the present disclosure, that a computer system 100 may first obtain a user selection of a region along an edge of a lung and selectively apply an edge detection filter to the user-selected regions while refraining from applying the edge detection filter to other portions of the images.

In some instances, the computer system 100 is configurable to trim the ends of the selection of the portion(s) of the pixels along the high-contrast interface between the lungs 302 and the surrounding tissue by a predetermined amount, such as 2 mm or more or less. In some instances, trimming the selection reduces the occurrence of inadvertent selection of sharp edges and/or fissures at the ends of the selection.

In addition, or as an alternative, to utilizing user-selected pixel regions along the boundary of the lungs 302, a computer system 100 may be configured to automatically select regions of lung boundaries pursuant to detecting the first actual lung boundary in accordance with act 206. For instance, the computer system 100 may be configured to select pixels of boundary regions that satisfy contrast conditions with surrounding tissue, that satisfy predetermined curvature constraints (e.g., to avoid selection of sharp edges or fissures), and/or that satisfy length conditions (e.g., meeting or exceeding 5 mm in length).

In some embodiments, the pixels of the selected portion of the pixels along the high-contrast interface between the lungs 302 and the surrounding tissue may be connected to form the first actual boundary line pursuant to act 206. Such operations may be referred to as "stitching" operations to form the first actual boundary line. A representation of a first actual boundary line 316 is provided in FIG. 3. In some instances, pixels of adjacent portions of pixels along the high-contrast interface between the lungs 302 and the surrounding tissue are also stitched together, such as where two selected portions of pixels are within a predetermined proximity to one another (e.g., where their endpoints are sufficiently close).

In some instances, the computer system 100 may be configured to remove one or more actual boundary lines. For example, the computer system 100 may be configured to remove all actual boundary lines except for a longest actual boundary line such that PSI scores only become calculated using the longest actual boundary line. In other instances, multiple actual boundary lines are retained such that one or more PSI scores may be obtained based on each retained actual boundary line or section (e.g., to calculate a single PSI score formed from multiple parts, or to calculate separate PSI scores that form the basis for a composite PSI score). In this regard, a "first actual lung boundary" according to act 206 may comprise multiple actual lung boundary sections or segments (in one or multiple separate slices of the first set of CT images 304).

Referring again to FIG. 2, Act 208 associated with act 204 of flow diagram 200 includes determining a first approximated lung boundary within the first set of CT images 304. The first approximated lung boundary may extend about at least the first perimeter of the lung (about which the first actual lung boundary extends, which, as noted above, may comprise multiple segments or sections). The first approximated lung boundary may comprise a representation of a smooth lung boundary for the first perimeter of the lung (e.g., to roughly approximate a smooth lung boundary of a healthy lung). It will be appreciated, in view of the present disclosure, that the "first approximated lung boundary" of act 208 may comprise separate approximated lung boundaries sections or segments for each separate actual lung boundary section or segment that forms the first actual lung boundary described hereinabove with reference to act 206.

In some instances, the first approximated lung boundary is implemented as a smooth polynomial line (spline). For example, the computer system 100 may fit a spline to the selection of the portion(s) of pixels that form the first actual lung boundary (according to act 206). In some embodiments, multiple different polynomials can be generated utilizing different contours that provide different abilities to measure fine or large lung surface irregularity. For example, the contour fit parameters of the spline can be, in some embodiments, manually adjusted such that the spline may more closely match actual lung boundary or smooth over irregularities present therein by changing the contour parameters. In some instances, a contour fit is set at approximately a 20 mm setting, providing a relatively smooth spline that allows for accurate detection and quantification of a broad range of lung surface irregularities.

Alternatively, or in addition, the overall bumpiness of the detected lung boundary can be directly quantified.

Figure 4:
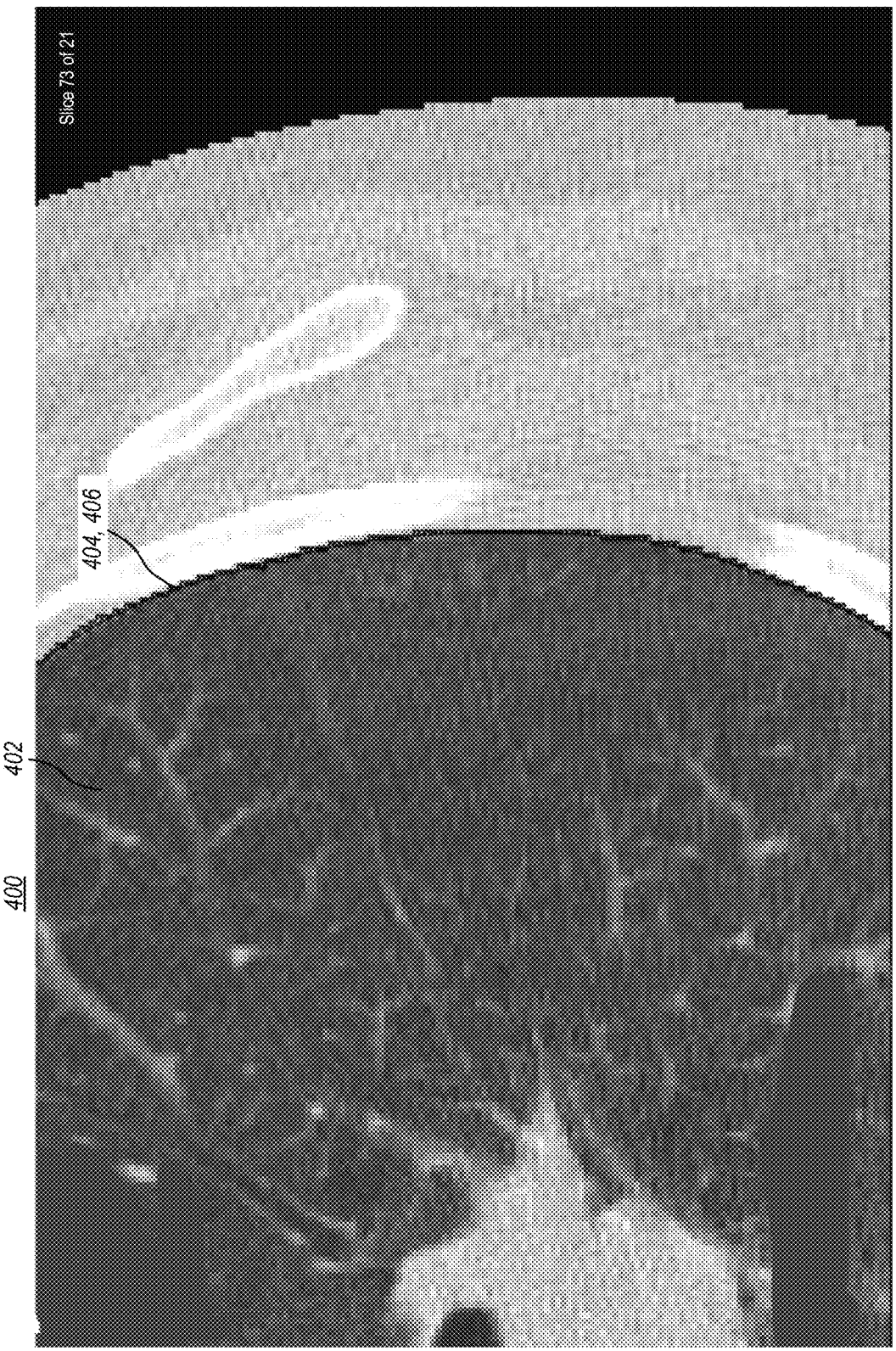
FIG. 4 illustrates an HRCT image of a lung not experiencing pulmonary fibrosis with an actual lung boundary and an approximated lung boundary depicted thereover.

In some embodiments, the computer system 100 is configurable to display representations of the first actual boundary line and the spline representing the approximated lung boundary in combination with one or more slices of the first set of CT images 304. FIG. 4 illustrates an HRCT image 400 of a lung 402 not experiencing pulmonary fibrosis with an actual lung boundary line 404 and an approximated lung boundary 406 depicted thereover. As is evident from FIG. 4, the actual lung boundary line 404 and the approximated lung boundary line 406 substantially overlap one another, indicating that the lung 402 does not comprise a bumpy or irregular surface. While not shown, similar results were observed at multiple different slices. As will be shown hereinafter, such an arrangement of an actual lung boundary line 404 and an approximated lung boundary line 406 may result in a relatively low PSI score, which may indicate a low degree or absence of pulmonary fibrosis, particularly when quantified in the aggregate (e.g., as a mean PSI score from a plurality of separate slices).

Figure 5:
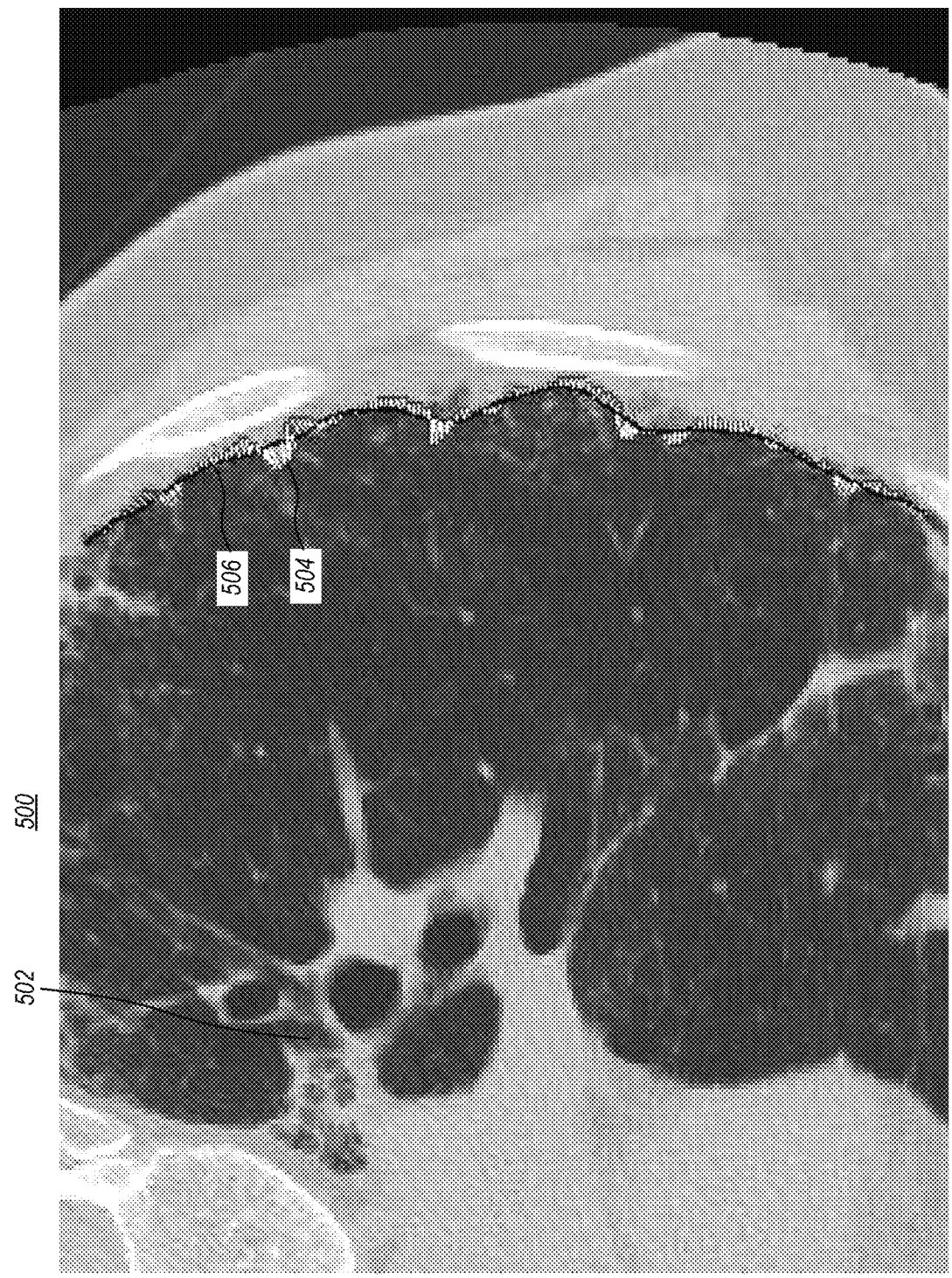
FIG. 5 illustrates an HRCT image of a lung that is experiencing idiopathic pulmonary fibrosis (IPF) with an actual lung boundary and an approximated lung boundary depicted thereover.

By comparison, FIG. 5 illustrates an HRCT image 500 of a lung 502 that is experiencing idiopathic pulmonary fibrosis (IPF) with an actual lung boundary line 504 and an approximated lung boundary 506 depicted thereover. As is evident from FIG. 5, the actual lung boundary line 504 diverges from and repeatedly intersects with the approximated lung boundary line 506. The actual lung boundary line 504 follows the bumpy and/or irregular surface of the lung 502 experiencing IPF, and the irregularity of the surface represented by the actual lung boundary line 504 is evident when compared with the approximated lung boundary line 506 (which, as noted above, may be regarded as representative of a smoother lung surface). As will be shown hereinafter, such an arrangement of an actual lung boundary line 504 and an approximated lung boundary line 506 may result in a relatively high PSI score, which may indicate a high degree or presence of pulmonary fibrosis.

The differences between an actual lung boundary line (e.g., actual lung boundary line 504) and an approximated lung boundary line (e.g., approximated lung boundary line 506) may provide a basis for determining a PSI score. Referring again to FIG. 2, act 210 associated with act 204 of flow diagram 200 includes determining the first PSI score for the lung using inputs based on the first actual lung boundary and the first approximated lung boundary.

In some embodiments, the PSI score is determined based on distances between the actual lung boundary line and the spline (or approximated lung boundary line) for each pixel within the selection of the portion of the pixels that forms the actual lung boundary line. In some instances, the distance between the detected lung boundary and spline is measured on a pixel-by-pixel basis.

Figure 6:
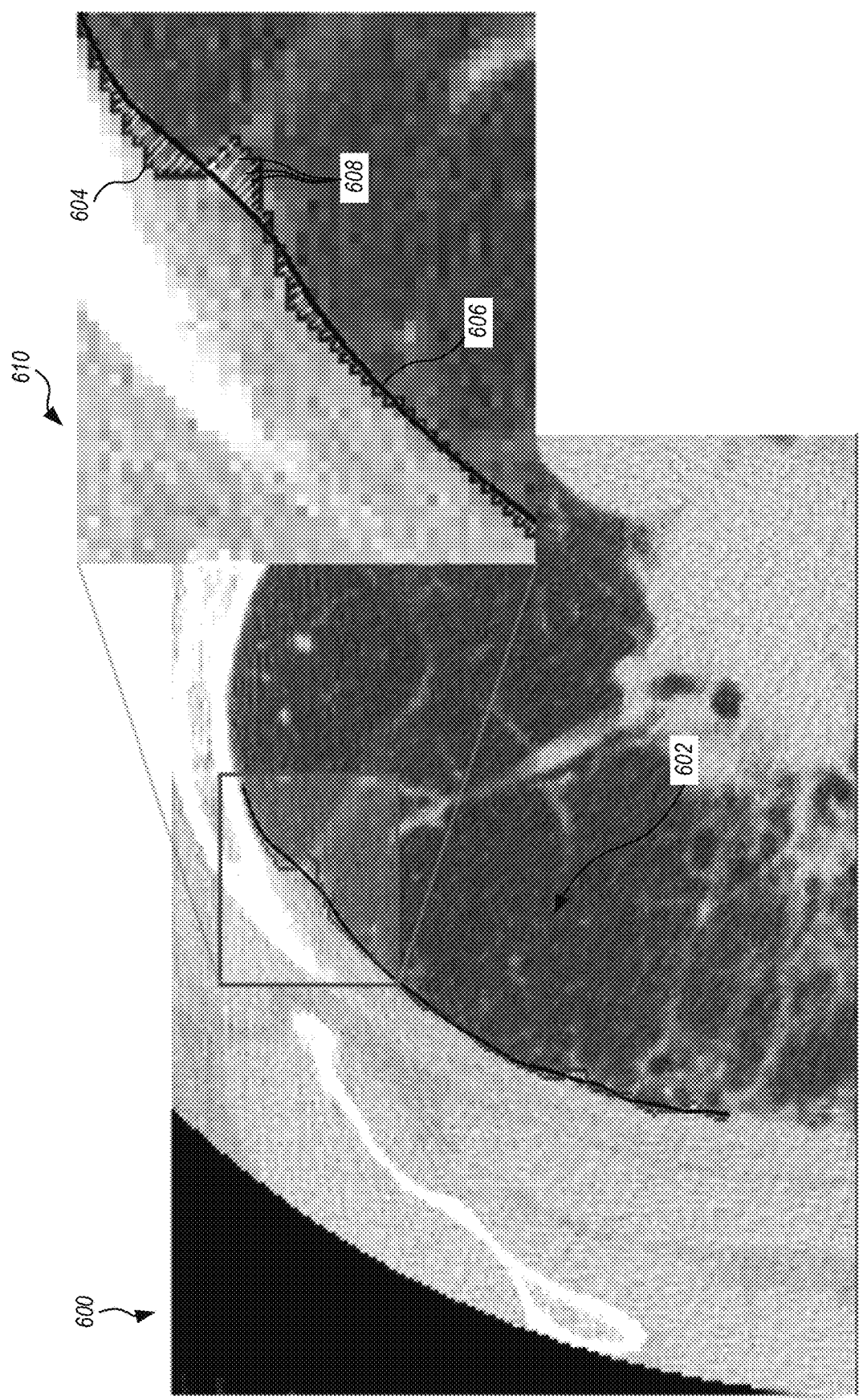
FIG. 6 illustrates an HRCT image of a lung that is experiencing IPF and includes a close-up view of an actual lung boundary, approximated lung boundary, and distance indicators between the pixels of the actual lung boundary and the approximated lung boundary.

For example, FIG. 6 illustrates an HRCT image 600 of a lung 602 that is experiencing IPF and includes a close-up view 610 of an actual lung boundary line 604, approximated lung boundary 606, and distance indicators 608 between the pixels of the actual lung boundary line 604 and the approximated lung boundary 606. The close-up view 610 shows that the distance indicators 608 indicate measured distance between the actual lung boundary line 604 and the approximated lung boundary 606 (e.g., spline) for at least some of the pixels that form the actual lung boundary line 604 (e.g., pixels that were stitched together to form the actual lung boundary line 604).

The distances represented in FIG. 6 by the distance indicators 608 may be combined in various ways to provide PSI scores. For example, in some embodiments, a mean and/or standard deviation of the distances ($d_i$, i=1, ..., n) are calculated and optionally multiplied by a multiplier (e.g., a multiplier, k, to provide a PSI score in desired units, such as tenths of millimeters) to calculate the PSI score by Mean Method or SD Method, respectively. Example mathematical formulas defining the PSI scores are as follows:

$$PSI \text{ Score based on Mean Method} = k \times \bar{d} = \frac{k}{n}\sum_{i=1}^{n} d_i$$

$$PSI \text{ Score based on SD Method} = k\sqrt{\frac{1}{n-1}\sum_{i=1}^{n}(d_i - \bar{d})^2}$$

Larger distances between the actual lung boundary line and spline may lead to larger PSI scores. Highly irregular lung surfaces (e.g., as shown in FIGS. 5 and 6) may be associated with larger variations in distances between the detected lung boundary and the spline and may increase the PSI scores. Small differences between the detected lung boundary and spline (e.g., as shown in FIG. 4), and therefore lower PSI scores, may be expected in individuals with a smooth lung surface who are not experiencing pulmonary fibrosis.

In some embodiments, the distances are adjusted before calculating a PSI score. In some embodiments, the distances between the actual lung boundary line and the approximated lung boundary (e.g., spline) are adjusted exponentially (e.g. squared), which emphasizes larger distances (and corresponding irregularity) and deemphasize smaller distances that can be found with smooth lung surfaces. Alternative mathematical adjustments (e.g. log transformation) to the distances may further affect the PSI score. A weighted mean of these distance measurements (or adjusted distance measurements) may be used to account for the length of the detected lung boundary, such that values from short or long detected lung boundaries can be directly compared. A standard deviation of the adjusted measurements may provide information both on overall maximal distances and the range of variance of the distances, and also may account for the measurements for the length of the detected lung boundary. Increased maximal distance between the lines is may be associated with increased fibrosis, and increased variance in the distance measurements may correspond to increasing surface irregularity.

As indicated above, in some instances, PSI scores may be determined using different edge detection sensitivity levels, which may result in the detection of different actual lung boundary lines and different approximated lung boundaries. For example, different PSI scores may be automatically determined based on distances between actual lung boundary lines and approximated lung boundary lines obtained according to multiple (e.g., 12) different edge sensitivity levels. In some instances, the detected actual lung boundary line and corresponding spline at the sensitivity level that provides the highest PSI score (e.g., by any method) may be depicted on a user interface (e.g., user interface 300). The sensitivity level corresponding to the highest PSI score, as well as the highest PSI score, may also be recorded and/or visually displayed (e.g., within data window 312 of user interface 300, FIG. 3).

Accordingly, in some instances, a user may review the images (e.g., by reviewing close-up views of one or more detected actual lung boundaries, as shown in FIG. 6), the approximated lung boundaries, and/or the PSI scores to confirm that the detected lung boundary and corresponding scores are appropriate. Any information related to the PSI scores or any components/data used to obtain them may become stored within local or remote storage (e.g., as data 112 of storage 108). In some instances, if the user does not think that the detected lung boundary or measurements appear appropriate (e.g., where the user recognizes that spline, attenuation, thresholding, and/or other parameters should be modified to obtain a more accurate PSI score), the PSI score(s) may be discarded, such as by scrolling to a different slice or selecting the segmentation tool, choosing another location for selection of pixels to form new actual lung boundary and for calculation of new measurements.

In other implementations, the area between the curves (ABC, area between the actual lung boundary line and the spline) can be used as an alternative to or in combination with the distance measurements described above as a basis for a PSI score. The ABC may be divided by the length of the actual lung boundary line to account for differences in length between different segments.

As indicated hereinabove, a user (or computer system 100) may select multiple selections of pixels along a lung boundary (e.g., whether in one or multiple slices of the set of CT images). For example, in some instances, a computer system 100 may enforce a requirement for the user to obtain multiple actual lung boundary lines for generating PSI scores to provide broad sampling of the surfaces of the lung. In some instances, distance measurements based on each separate actual lung boundary line are combined to generate a single PSI score for use as the first PSI score according to act 204. In other instances, separate PSI scores are generated based on each respective actual lung boundary line, and the separate PSI scores may be combined to generate a composite PSI score (e.g., by averaging, weighted averaging, etc.) for use as the first PSI score according to act 204.

As noted hereinabove, PSI scores may be used to perform longitudinal analysis of the treatment response and/or disease progression of pulmonary fibrosis. In this regard, referring again to FIG. 2, act 212 of flow diagram 200 includes obtaining a second set of CT images of the lung, the second set of CT images of the lung being associated with a second timepoint. The second timepoint may be different than the first timepoint associated with the first set of CT images 304 described hereinabove with reference to act 202. For example, the second timepoint may comprise one or more timepoints that are subsequent to or previous to the first timepoint.

Act 214 of flow diagram 200 includes determining a second PSI score for the lung. Act 214 for determining the second PSI score may employ techniques similar to those described hereinabove for determining the first PSI score, such as detecting a second actual lung boundary of the lung within the second set of CT images (which may extend about the same or different perimeter(s) as the first actual lung boundary associated with act 206), determining a second approximated lung boundary within the second set of CT images (e.g., one or more splines), and determining the second PSI score for the lung using inputs based on the second actual lung boundary and the second approximated lung boundary (e.g., based on per-pixel measured distances between the second approximated lung boundary and the second actual lung boundary).

Act 216 of flow diagram 200 includes assessing pulmonary fibrosis treatment response or disease progression for the lung based on the first PSI score and the second PSI score. A comparison of the second PSI score to the first PSI score may help medical practitioners make intelligent treatment decisions about pulmonary fibrosis. For example, where the second timepoint is later than the first timepoint, a second PSI score that is higher than a first PSI score may indicate that pulmonary fibrosis is progressing, and the magnitude of the difference between the scores may be indicative of the rate of progression. Such a difference between a second PSI score and a first PSI score may also indicate that a treatment applied between the first timepoint and the second timepoint is ineffective or exacerbating pulmonary fibrosis. Conversely, where the second timepoint is later than the first timepoint, a second PSI score that is lower than a first PSI score may indicate that pulmonary fibrosis is regressing or being effectively treated. Accordingly, at least some embodiments of the present disclosure may provide substantially continuous, usable metrics (e.g., PSI scores) for assessing disease progression and/or treatment response of pulmonary fibrosis.

Figure 7:
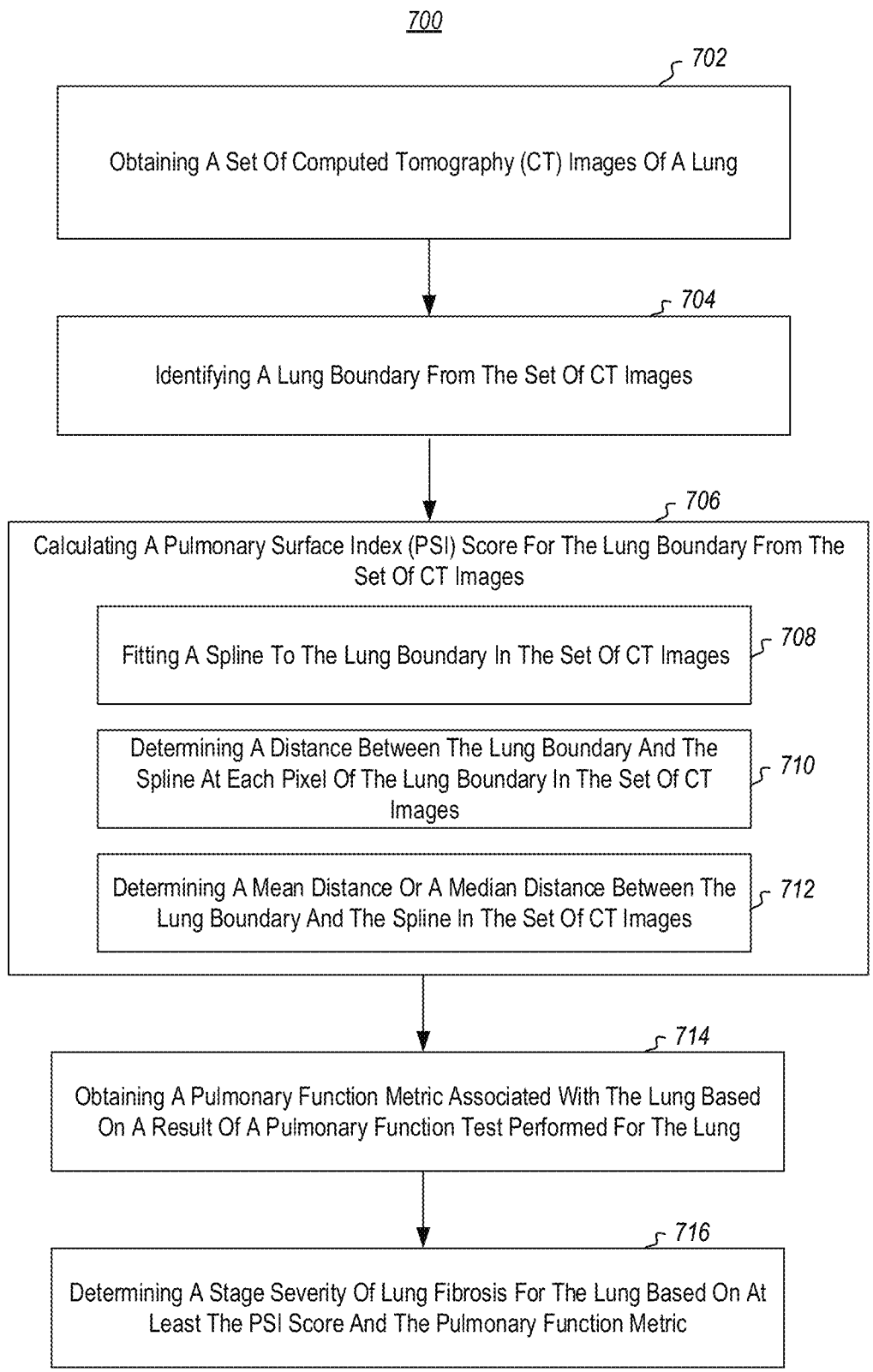
FIG. 7 illustrates an example flow diagram depicting acts associated with ascertaining stage severity of pulmonary fibrosis.

Although the present disclosure has focused, in at least some respects, on implementations in which PSI scores for multiple timepoints are obtained for longitudinal analysis of pulmonary fibrosis (e.g., for assessing treatments response or disease progression), it should be noted that, in some embodiments, PSI scores are obtained in association with a single timepoint (e.g., for disease staging). For example, FIG. 7 illustrates an example flow diagram 700 depicting acts associated with ascertaining stage severity of pulmonary fibrosis. Similar to flow diagram 200 described hereinabove, no particular ordering is required unless specifically stated or required because an act is dependent on another act being completed prior to the act being performed. Furthermore, it should be noted that not all acts represented in flow diagram 700 are essential for ascertaining stage severity of pulmonary fibrosis.

Act 702 of flow diagram 700 includes obtaining a set of computed tomography (CT) images of a lung. The set of CT images of act 702 may correspond in at least some respects to the first and/or second sets of CT images described hereinabove with reference to acts 202 and 212 of flow diagram 200 of FIG. 2.

Act 704 of flow diagram 700 includes identifying a lung boundary from the set of CT images. The lung boundary from the set of CT images of act 704 may correspond in at least some respects to the first actual lung boundary described hereinabove with reference to act 206 of flow diagram 200 of FIG. 2.

Act 706 of flow diagram 700 includes calculating a Pulmonary Surface Index (PSI) score for the lung boundary from the set of CT images. Calculating a PSI score in accordance with act 706 may rely at least in part on techniques described hereinabove for calculating a first PSI score in accordance with act 204 of flow diagram 200 of FIG. 2 described hereinabove. For example, FIG. 7 illustrates that calculating a PSI score for the lung boundary from the set of CT images according to act 706 may be associated with various additional acts. For example, act 708 associated with act 706 of flow diagram 700 includes fitting a spline to the lung boundary in the set of CT images. The spline may correspond to the spline(s) described hereinabove as representative of an approximated lung boundary of act 208 of flow diagram 200 of FIG. 2.

Also, act 710 associated with act 706 of flow diagram 700 includes determining a distance between the lung boundary and the spline at each pixel of the lung boundary in the set of CT images. The distance(s) between the lung boundary and the spline may be similar to the distance between the actual lung boundary line and the expected lung boundary line described hereinabove with reference to act 210 of flow diagram 200 of FIG. 2. Furthermore, Act 712 associated with act 706 of flow diagram 700 includes determining a mean distance or a median distance between the lung boundary and the spline in the set of CT images. The mean or median distance may be established as the PSI score in accordance with act 706.

Act 714 of flow diagram 700 includes obtaining a pulmonary function metric associated with the lung based on a result of a pulmonary function test performed for the lung. The pulmonary function metric may take on various forms. For example, in some embodiments, the pulmonary function metric may comprise a measure of one or more spirometry tests (e.g., pulmonary function tests), such as forced expiratory volume (FEV), forced vital capacity (FVC), and/or diffusing capacity of the lung for carbon monoxide (DLCO).

A measure of FVC is a measure of the volume of air that can forcibly be blown out by a subject after full inspiration (e.g., measured in liters and may be compared with a reference value as a percentage). A measure of FEV is corresponds to the volume of air that can be forcibly blown out by a subject in a fixed time period (e.g., one second) after full inspiration. A measure of DLCO corresponds to the carbon monoxide uptake from a single inspiration of a subject within a predefined breath-hold time period (e.g., ten seconds). To measure DLCO, subject typically inhales a test gas mixture that includes an inert tracer gas and carbon monoxide (e.g., less than 1%). The exhaled carbon monoxide is subtracted from the known amount of carbon monoxide that was inhaled to determine the amount transferred during the breath-hold time period.

In some instances, the pulmonary function metric may comprise one or more other scores that rely at least in part on pulmonary function tests, such as a GAP score or a du Bois score.

A GAP score assesses gender, age, and physiological factors (e.g., FVC, DLCO) to provide a rough staging system for IPF. The GAP index assigns points to certain predictors of IPF progression. For instance, the male gender is assigned 1 point, whereas the female gender is assigned 0 points. An age of below 60 is assigned 0 points, an age of 61-65 is assigned 1 point, and an age above 65 is assigned 2 points. An FVC that is greater than 75% (as compared with a reference or predicted value) is assigned a score of 0, while an FVC that is between 50% and 75% is assigned a score of 1, and an FVC that is less than 50% is assigned a score of 2. A DLCO score that is greater than 55% (as compared with a reference or predicted value) is assigned a score of 0, a DLCO score that is between 36% and 55% is assigned a score of 1, a DLCO score that is lower than or equal to 35% is assigned a score of 2, and a score of 3 is assigned to cases wherein a subject is unable to perform a DLCO test (which requires breath-holding). Under the GAP staging system, a sum of points that is equal to or less than 3 is associated with stage I and a 1-year mortality rate of 5.6%, a 2-year mortality rate of 10.9%, and a 3-year mortality rate of 16.3%. A sum of points that is equal to 4 or 5 is associated with stage II and a 1-year mortality rate of 16.2%, a 2-year mortality rate of 29.9%, and a 3-year mortality rate of 42.1%. A sum of points that is equal to 6, 7, or 8 is associated with stage III and a 1-year mortality rate of 39.2%, a 2-year mortality rate of 62.1%, and a 3-year mortality rate of 76.8%.

A du Bois score assigns points to various risk factors, such as age, respiratory hospitalization history (e.g., within the preceding 6 months), predicted baseline FVC, and 24-week change in predicted FVC to provide an expected 1-year probability of death.

Act 716 of flow diagram 700 includes determining a stage severity of lung fibrosis for the lung based on at least the PSI score and the pulmonary function metric. As noted hereinabove, a higher PSI score may be indicative of a more advanced stage of pulmonary fibrosis. In some instances, combining a PSI score with other metrics associated with lung health may provide a robust, multi-component methodology useful for staging pulmonary fibrosis. For example, the PSI score may be mathematically combined with the pulmonary function metric (e.g., FEV, FVC, DLCO, GAP score, du Bois score, and/or others) to provide a composite score or value for determining the stage severity of lung fibrosis, such as by applying the pulmonary function metric as a weighting factor, multiplier, denominator, etc. In some instances, medical practitioners may consider the pulmonary function metric as a modifying factor (e.g., an aggravating factor, or a mitigating factor) when assessing a pulmonary function metric to stage pulmonary fibrosis, or, conversely, medical practitioners may consider one or more pulmonary function metrics as a modifying factor when assessing a PSI score to stage pulmonary fibrosis. It will be appreciated that one or more pulmonary function metrics may be considered in combination with one or more PSI scores associated with different timepoints to assess treatment response and/or disease progression of pulmonary fibrosis as described hereinabove.

Furthermore, in some instances, a PSI score may be combined with other lung morphometric measurements (whether from medical images or not), the presence or absence and/or identification of signs of pulmonary hypertension on medical images, an individual's age, gender and/or body mass index, and/or one or more blood, urine or salivary laboratory tests, and/or with a physical measure of lung stiffness pursuant to staging, assessing treatment response, or assessing disease progression of pulmonary fibrosis. In some instances the PSI score is combined with other quantitative lung measurements, including the amount or percentage of normal lung, abnormal lung, lung opacities (e.g. all lung opacities, groundglass opacities, honeycombing), bronchiectasis, and/or volume of a lung or lobe.

It should be appreciated that the foregoing systems and methods are not limited to being practiced using HRCT (1.25 mm) images, as demonstrated in the various figures and descriptions provided hereinabove. The disclosed systems and methods can beneficially utilize regular chest CT images (2.5 mm, or >1.5 mm) to similarly ascertain the stage severity of pulmonary fibrosis and/or ascertain pulmonary fibrosis disease progression or treatment response.

Figure 8:
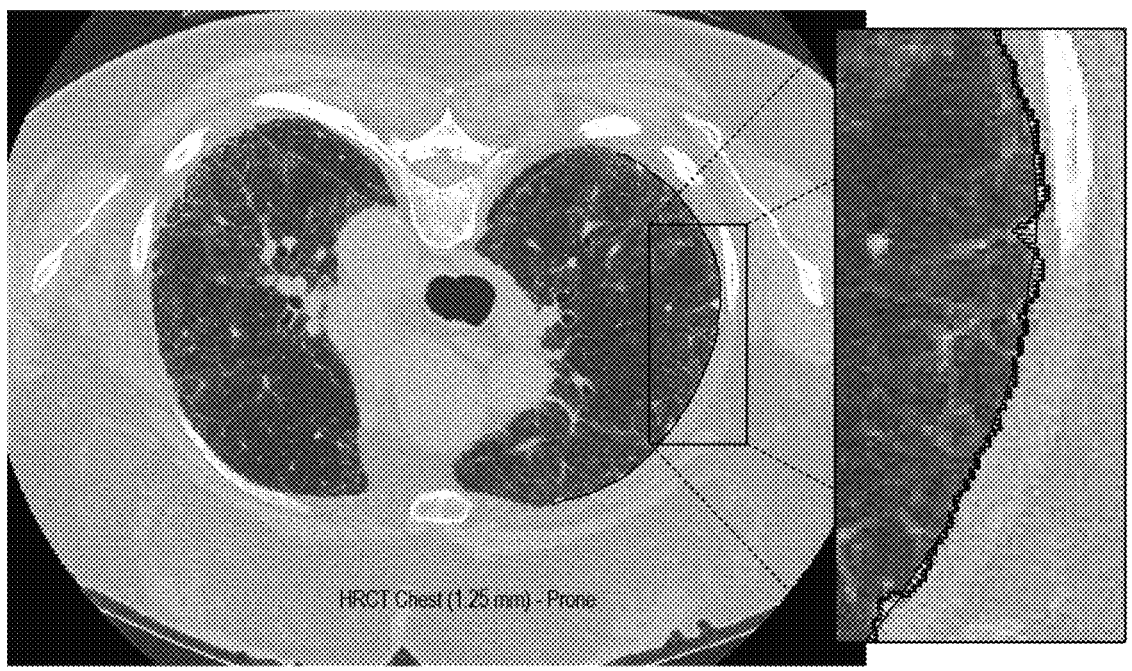
FIG. 8 illustrates an HRCT (1.25 mm) image of a lung and includes a close-up view of an actual lung boundary, approximated lung boundary, and distance indicators between the pixels of the actual lung boundary and the approximated lung boundary.
Figure 9:
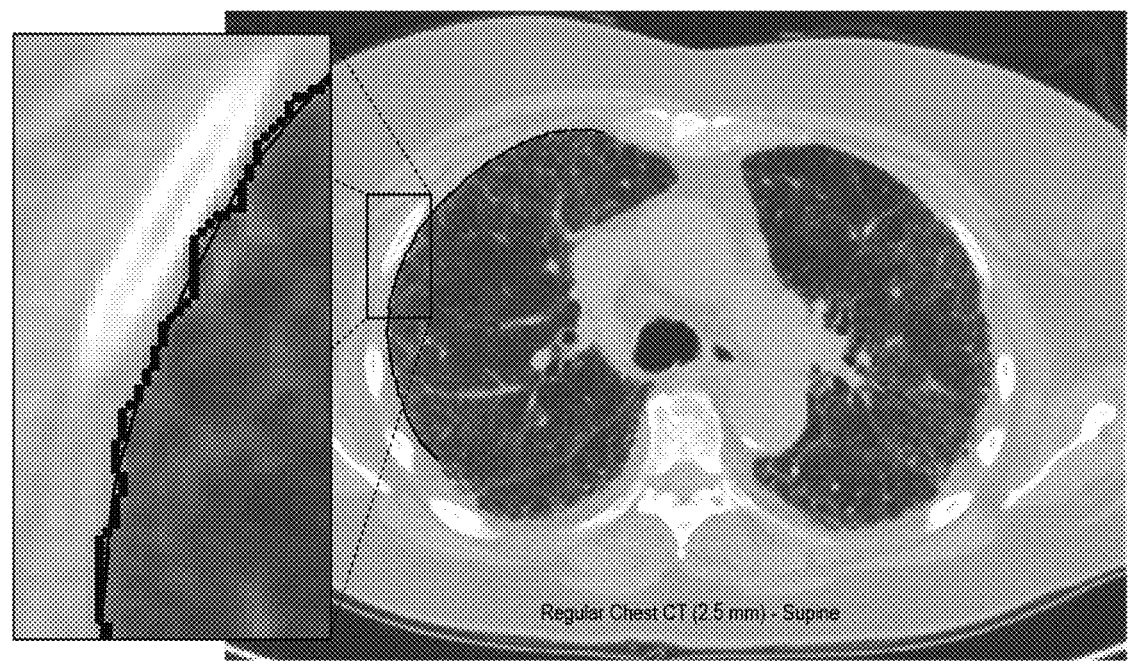
FIG. 9 illustrates a regular chest CT (2.5 mm) image of the lung from FIG. 8 and includes a close-up view of an actual lung boundary, approximated lung boundary, and distance indicators between the pixels of the actual lung boundary and the approximated lung boundary, demonstrating that the systems and methods disclosed herein can be practiced on regular chest CT images as well as HRCT images.

FIG. 8, for example, illustrates an HRCT (1.25 mm) image of a lung and includes a close-up view of an actual lung boundary, approximated lung boundary, and distance indicators between the pixels of the actual lung boundary and the approximated lung boundary. FIG. 9 illustrates a regular chest CT (2.5 mm) image of the lung from FIG. 8 and includes a close-up view of an actual lung boundary, approximated lung boundary, and distance indicators between the pixels of the actual lung boundary and the approximated lung boundary, demonstrating that the systems and methods disclosed herein can be practiced on regular chest CT images as well as HRCT images.

It should also be appreciated that while the drawings and associated descriptions are focused on calculating a PSI score from a lung boundary observed in a single CT slice, the accuracy of the PSI score, as indicative of the stage severity of pulmonary fibrosis, increases when a PSI score is calculated from multiple slices. In some embodiments, the overall PSI score for a given lung is determined as an average or median score from two slices, preferably from three or more slices. The plurality of slices are preferably not adjacent slices but are instead separated from each other by at least one intervening slice where the PSI score is not calculated.

Disclosed embodiments may comprise or utilize a special purpose or general-purpose computer including computer hardware, as discussed in greater detail below. Disclosed embodiments also include physical and other computer-readable media for carrying or storing computer-executable instructions and/or data structures. Such computer-readable media can be any available media that can be accessed by a general purpose or special purpose computer system.

Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: physical computer-readable storage media (e.g., hardware storage devices) and transmission computer-readable media.

Physical computer-readable storage media includes hardware storage devices such as RAM, ROM, EEPROM, CD-ROM or other optical disk storage (such as CDs, DVDs, etc.), magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry program code in the form of computer-executable instructions or data structures, and which can be accessed by a general purpose or special purpose computer. Combinations of the above are also included within the scope of computer-readable media.

Further, upon reaching various computer system components, program code means in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (e.g., a "NIC"), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general-purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Disclosed embodiments may comprise or utilize cloud computing. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, wearable devices, and the like. The invention may also be practiced in distributed system environments where multiple computer systems (e.g., local and remote systems), which are linked through a network (either by hardwired data links, wireless data links, or by a combination of hardwired and wireless data links), perform tasks. In a distributed system environment, program modules may be located in local and/or remote memory storage devices.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Application-specific Standard Products (ASSPs), System-on-a-chip systems (SOCs), Complex Programmable Logic Devices (CPLDs), central processing units (CPUs), graphics processing units (GPUs), and/or others.

As used herein, the terms "executable module," "executable component," "component," "module," or "engine" can refer to hardware processing units or to software objects, routines, or methods that may be executed on one or more computer systems. The different components, modules, engines, and services described herein may be implemented as objects or processors that execute on one or more computer systems (e.g. as separate threads).

Although the subject matter described herein is provided in language specific to structural features and/or methodological acts, it is to be understood that the subject matter defined in the appended claims is not necessarily limited to the described features or acts so described. Rather, the described features and acts are disclosed as example forms of implementing the claims.

Unless defined otherwise, all technical and scientific terms used herein have the same meaning as commonly understood by one of ordinary skill in the art to which the present disclosure pertains.

Various alterations and/or modifications of the inventive features illustrated herein, and additional applications of the principles illustrated herein, which would occur to one skilled in the relevant art and having possession of this disclosure, can be made to the illustrated embodiments without departing from the spirit and scope of the invention as defined by the claims, and are to be considered within the scope of this disclosure. Thus, while various aspects and embodiments have been disclosed herein, other aspects and embodiments are contemplated. While a number of methods and components similar or equivalent to those described herein can be used to practice embodiments of the present disclosure, only certain components and methods are described herein.

It will also be appreciated that systems and methods according to certain embodiments of the present disclosure may include, incorporate, or otherwise comprise properties or features (e.g., components, members, elements, parts, and/or portions) described in other embodiments. Accordingly, the various features of certain embodiments can be compatible with, combined with, included in, and/or incorporated into other embodiments of the present disclosure. Thus, disclosure of certain features relative to a specific embodiment of the present disclosure should not be construed as limiting application or inclusion of said features to the specific embodiment unless so stated. Rather, it will be appreciated that other embodiments can also include said features, members, elements, parts, and/or portions without necessarily departing from the scope of the present disclosure.

Moreover, unless a feature is described as requiring another feature in combination therewith, any feature herein may be combined with any other feature of a same or different embodiment disclosed herein. Furthermore, various well-known aspects of illustrative systems, methods, apparatus, and the like are not described herein in particular detail in order to avoid obscuring aspects of the example embodiments. Such aspects are, however, also contemplated herein.

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the methods, products, devices, and apparatus disclosed herein may be made without departing from the scope of the disclosure or of the invention, which is defined in the appended claims. All changes which come within the meaning and range of equivalency of the claims are to be embraced within their scope.

The invention claimed is:

1. A computer-implemented method for ascertaining stage severity of pulmonary fibrosis, the method comprising:
    obtaining a set of computed tomography (CT) images of a lung;
    identifying a lung boundary from the set of CT images, the lung boundary comprising an outer portion of the lung that extends about a perimeter of the lung and is in contact with one or more adjacent organs or tissues;

calculating a Pulmonary Surface Index (PSI) score for the lung boundary from the set of CT images, wherein calculating the PSI score for the lung boundary comprises:
    fitting a spline to the lung boundary in the set of CT images;
    determining a distance between the lung boundary and the spline at each pixel of the lung boundary in the set of CT images; and
    determining a mean distance or a median distance between the lung boundary and the spline in the set of CT images;
obtaining a pulmonary function metric associated with the lung based on a result of a pulmonary function test performed for the lung; and
determining a stage severity of lung fibrosis for the lung based on at least the PSI score for the lung boundary and the pulmonary function metric.

2. The computer-implemented method of claim 1, wherein identifying the lung boundary from the set of CT images is performed according to a predetermined attenuation range for the set of CT images.

3. The computer-implemented method of claim 1, wherein the spline comprises a contour fit of at least 20 mm.

4. The computer-implemented method of claim 1, wherein calculating the PSI score further comprises automatically trimming the identified lung boundary by a predetermined amount.

5. The computer-implemented method of claim 1, wherein the pulmonary function metric associated with the lung comprises a measure of forced expiratory volume (FEV) associated with the lung.

6. The computer-implemented method of claim 1, wherein the pulmonary function metric associated with the lung comprises a measure of forced vital capacity (FVC) associated with the lung.

7. The computer-implemented method of claim 1, wherein the pulmonary function metric associated with the lung comprises a measure of diffusing capacity of the lung for carbon monoxide (DLCO) associated with the lung.

8. The computer-implemented method of claim 1, wherein the pulmonary function metric associated with the lung comprises a GAP score or a du Bois score associated with the lung.

9. The computer-implemented method of claim 1, wherein the PSI score for the lung boundary is representative of retraction of an outer surface of the lung.

\* \* \* \* \*